United States Patent [19]
Mojena

[11] Patent Number: 5,457,823
[45] Date of Patent: Oct. 17, 1995

[54] URINE SPECIMEN COLLECTOR FOR USE BY FEMALES

[76] Inventor: Gregory L. Mojena, Calle 10, Block 7-1, Sabana Gardens, Carolina, Puerto Rico, 00983

[21] Appl. No.: 335,344

[22] Filed: Nov. 3, 1994

[51] Int. Cl.⁶ .................................................. A47K 11/12
[52] U.S. Cl. .................................................. 4/144.2
[58] Field of Search .................... 4/144.1–144.4; 128/761; 604/329; 383/8, 9, 34

[56] References Cited

U.S. PATENT DOCUMENTS

| | | |
|---|---|---|
| 976,883 | 11/1910 | Keagy et al. . |
| 3,403,410 | 10/1968 | Benzel et al. ............................ 4/144.2 |
| 3,575,225 | 4/1971 | Muheim . |
| 3,923,040 | 12/1975 | Beach ..................................... 4/144.2 X |
| 3,964,111 | 6/1976 | Packer . |
| 4,305,161 | 12/1981 | Diaz . |
| 4,453,938 | 6/1984 | Brendling . |
| 4,500,314 | 2/1985 | Brendling . |
| 4,608,046 | 8/1986 | Towfigh . |
| 4,681,573 | 7/1987 | McGovern et al. . |
| 4,696,067 | 9/1987 | Woodward . |
| 4,751,751 | 6/1988 | Reno . |
| 4,937,890 | 7/1990 | Tafur . |
| 5,009,236 | 4/1991 | Brothers . |
| 5,353,805 | 10/1994 | Mojena ................................... 128/761 |

*Primary Examiner*—Charles E. Phillips
*Attorney, Agent, or Firm*—Oblon, Spivak, McClelland, Maier & Neustadt

[57] ABSTRACT

A urine collector for use by females includes a funnel-like bag having a small end removably sealed to the neck of a specimen collector and a large end connected to the resilient legs of a tong-like member. One end of the legs are connected together so as to prevent their movement apart and the other ends of the legs are pivoted together. Handles are connected to the other ends of the legs and when moved in opposite directions tend to spread the legs which bow away from each other due to their resilience and the interconnection of the legs at the one end. After the legs and bag in unstressed condition have been positioned between the user's labia and beneath the urethra the handles are operated to bow the legs and push the labia clear of the stream. The handles are spaced from the legs of the tong-like member so that the user's hands are free of splashing and the entire stream flows into the container untainted by bacteria normally residing on the labia.

7 Claims, 2 Drawing Sheets

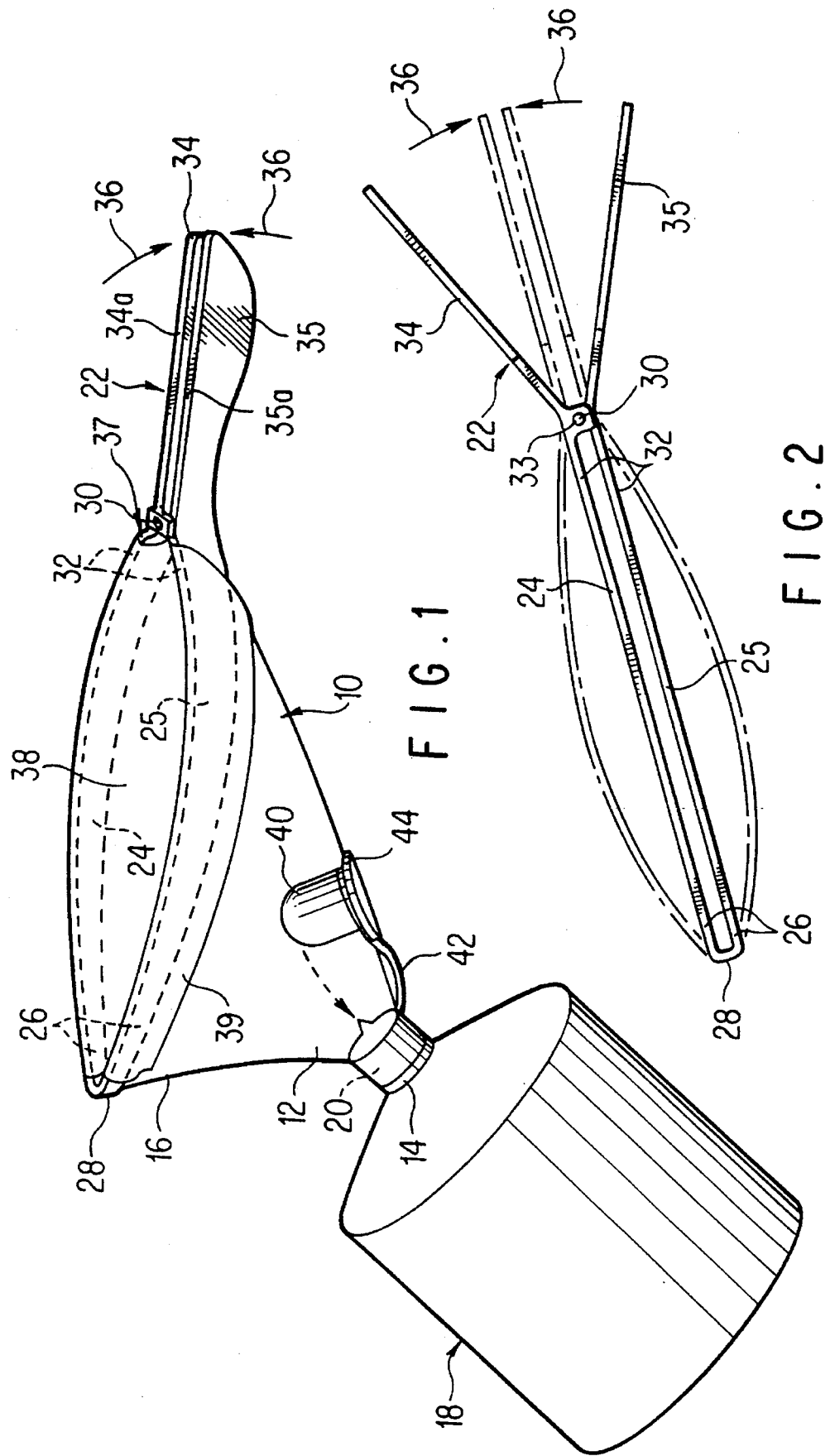

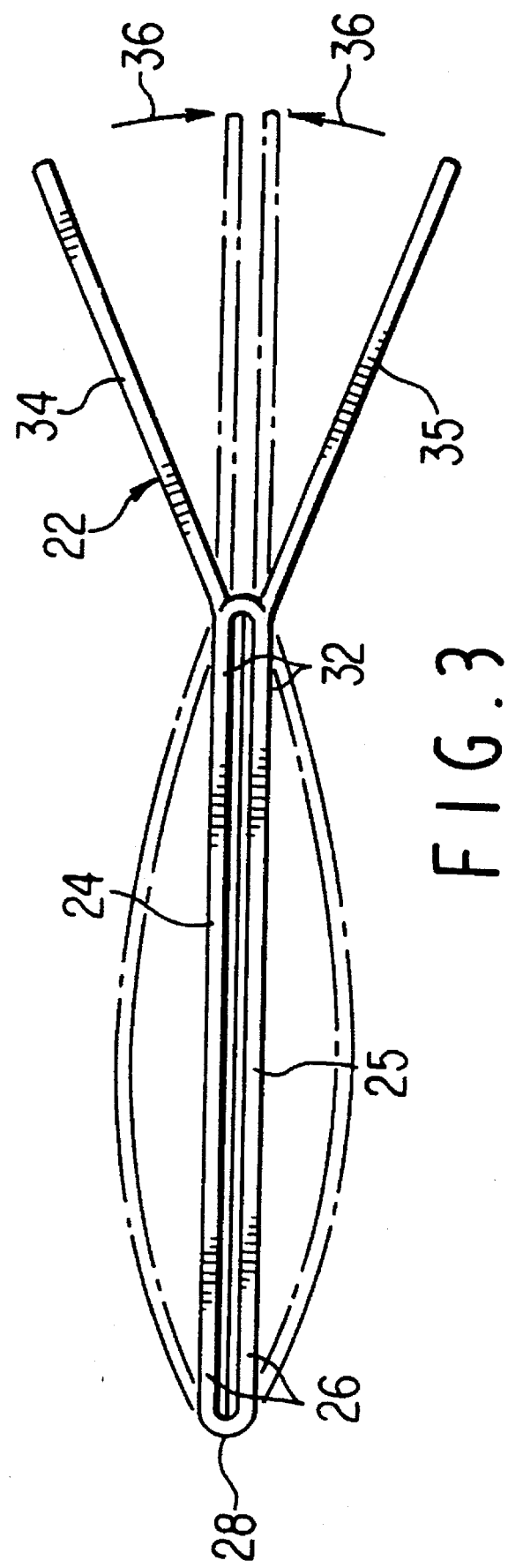

URINE SPECIMEN COLLECTOR FOR USE BY FEMALES

FIELD OF THE INVENTION

This invention relates to urine specimen collectors and more particularly to specimen collectors especially adapted to use by females.

BACKGROUND OF THE INVENTION

For diagnostic purposes the urine of both males and females must be collected for analysis. For a male this is a simple matter since he merely urinates through his penis directly into the collector. Urinating directly into a container is often the only procedure available to females but because the convenience of a penis is not available to a woman, the best she can do is to place the opening of the collector approximately in line with the outlet of her urethra. Because a woman's stream is not well confined, almost invariably the stream hits her fingers which is, of course, unpleasant. Furthermore, because the urethra of a woman is bracketed by the major and minor labia, as the stream flows from the urethra to a place of deposit such as a urine collector or a commode, the stream flows over the labia and entrains bacteria and the like found on the labia but not present in the stream as it flows from the urethra. During analysis, this foreign culture, found normally only on the labia, can give misleading readings as to the actual nature of the urine.

An object of the present invention is to provide a urine specimen collector for use by females which neatly collects a specimen with no danger of the stream striking the hand or fingers of the user. The urine specimen collector of the present invention is also useful for taking a urine specimen from a very ill female, who can't move from her bed or from an emergency room stretcher. By using the device of the present invention, a urine specimen can be taken without creating an inconvenience for the patient.

Another object of the invention is to provide a urine collector which, after location beneath the urethra, is manipulatable to open the wide end of a funnel-like bag into a substantial elliptical shape, having a width to ensure that the stream flows wholly into the open end of the funnel-like bag, and at the same time the labia are pushed apart so as to be entirely free of the urine stream issuing from the urethra.

BRIEF DESCRIPTION OF THE INVENTION

The invention comprises the combination of a funnel-like, urine impervious bag having an opening at its narrow end hermetically sealed to the open neck of a specimen receiver. The wide end of the bag is open and the sides of the opening are adhered to flexible legs of a tong-like member. The legs are connected to each other at their first ends and pivoted to each other at their second ends, with each of the second ends carrying a handle on the same side of the pivot as the leg to which the handle is attached. The handles extend angularly away from each other so that when they are squeezed together the flexible legs bow away from each other between the respective connected and pivoted ends to cause the open end of the funnel-shaped bag to define an elliptical shape. after the tong-like members, bag and container are placed between the legs of a user with the flexible legs of the tong-like member located between the labia and under the urethra, when the handles are squeezed together not only is a sufficiently wide opening in the bag provided beneath the urethra to ensure that the entire stream flows into the open end of the bag without splashing to its exterior, and at the same time the labia are pushed apart to ensure that they are clear of the stream so that it is untainted by bacteria on the labia.

It is contemplated that the combination of container, bag and tong-like element will be manufactured under sterile conditions and will be rolled together for encapsulation in a sterile container, usually of transparent flexible plastic material, which the user opens immediately prior to use. The bag has sealed therein a stopper which is easily manoeuvered into the open end of the container after use, and known tearable connectors are provided for separating the container and stopper from the bag. All of the components are made of inexpensive plastic and readily discarded following a single use.

BRIEF DESCRIPTION OF THE DRAWINGS

FIG. 1 is a perspective view of an entire assembly of the present invention;

FIG. 2 is a horizontal elevational view of the tong-like member of the invention showing in phantom how the legs of the member bow away from each other upon squeezing of the handles towards each other; and FIG. 3 is a top view of the assembly illustrating a further embodiment.

DETAILED DESCRIPTION OF THE PREFERRED EMBODIMENT

In accordance with the invention the urine specimen collector for use by females comprises a funnel-shaped, urine-impervious bag 10, preferably of clear flexible plastic sheet material having a narrow end 12 including an opening therein and a wide end 16. A urine specimen collector container 18 has a neck 20 having an opening therein around which the opening 14 at the narrow end 12 of the bag 10 is sealed.

In accordance with the invention, a tong-like member 22 is provided. The member 22 comprises a pair of resilient legs 24, 25 lying in a common plane. The legs 24, 25 have first ends 26 interconnected together at 28 so as to prevent any, substantial movement of the first ends 26 of the legs away from each other. A pivot portion 30 connects the second ends 32 of the legs 24 for relative movement of the second ends 32 about an axis 33 perpendicular to the common plane of the legs. Handles 34, 35 are connected to the second ends 32 of each of the legs 24, 25 on the same side of the pivot axis 33 as the leg to which it is attached. That is to say, the handle 34 and its leg 24 are located to the upper side of the pivot axis 33 in FIG. 2 whereas the handle 35 and leg 25 are located to the lower side of the pivot axis. As clearly seen in FIG. 2, with the resilient legs 24, 25 in their unstressed solid line positions of FIG. 2, the handles 34, 35 are normally angled away from each other so that a force on the handles squeezing them together, as indicated by the arrows 36, causes the legs 24 and 25 to pivot away from each other due to their resilience and their interconnection at 28 and at pivot axis 33. Therefore the legs 24 and 25 bow in opposite directions away from each other in the common plane of the legs, as should be clear in FIG. 2. The embodiment of FIG. 2 shows a pivot axis connection at 33. However, as illustrated in the top view of FIG. 3, the legs 24, 25 as well as the handles 34, 36 can be a molded one piece construction which provides for a continuous molded device.

As is apparent in FIG. 1, the wide end 16 of the bag 10 has an opening 38 therein of a length not greater than the length of the legs. The bag material on opposite sides of the opening 38 is fastened to the legs 24, 25 by any convenient means as, for example, by being folded over the legs, as shown at 39 in FIG. 1, and adhered to itself. The spacing between the legs 24, 25 in their solid-line unflexed condition of FIG. 2 is selected so that when the assembly is inserted between the legs of the user and beneath her urethra, the legs can be gently raised to a position between her labia and generally in line with the urethra. Now when the handles 34, 35 are squeezed together the legs 24, 25 are bowed away from each thus providing a clear path from the urethra into the open end of the bag while the labia are simultaneously engaged by the bowed legs to move the labia clear of the stream and prevent positively any taint of the stream by extraneous bacteria on the labia.

In accordance with the invention, the upper edges 34a, 35a of the respective handles 34, 35 lie in a plane spaced below a plane defined by the upper edges of the legs. This construction defines a kind of hump 37 which aids in the proper location of the assembly between the users legs while movement of the handles is not impeded by the woman's anatomy in that region.

In accordance with the invention, a stopper 40 may be molded to the interior of the bag 10. The stopper 40 is of a size to be sealingly received within the opening of the neck 20 of the collector 18. Thus, when the collector 18 has received the proper amount of a urine specimen, the user, with little effort and by manipulating the bag from the outside, inserts the stopper 40 into the open end of the collector. A plastic strip 42 has one end encircling a protruding end part 42 of the stopper 40 and an opposite end encircling the bag material where it extends over the open ended neck 14 of the container 18. After the stopper has been inserted into the neck, the plastic strip is easily torn away from both the stopper and the neck whereupon the bag and tong-like member are discarded.

Having fully described the invention, what is claimed is:

1. Urine specimen collector for use by females comprising a funnel-shaped, urine-impervious bag having a narrow end including an opening therein and a wide end, a urine specimen collector container having an open neck around which said opening at the narrow end of said bag is sealed, a tong-like member comprising a pair of resilient legs lying in a common plan, said legs having first ends interconnected together so as to prevent any substantial movement of said first ends away from each other, a pivot connecting the second ends of said legs together for relative movement about an axis perpendicular to said common plane, a handle connected to the second end of each of said legs whereby a force in opposite directions on said handles causes the second ends of said legs to pivot away from each other and the legs to bow in opposite directions in said common plane due to their resilience and the interconnection of said first ends of said legs, said wide end of said bag having an opening therein of a length not greater than the lengths of said legs, and means for sealingly connecting the wide end of said bag to said legs on opposite sides of said opening.

2. The collector of claim 1 including a stopper of a size to be sealingly received within the opening of said container, said stopper extending freely into said bag and being sealed at one end to said bag, said stopper being positioned that from the exterior of the bag it can be manipulated into the opening of said container to seal the same, and a tearable connector between said bag and the sealed end of the stopper.

3. The collector of claim 1, including a tearable connector between the neck of said container and the opening in the narrow end of said bag enabling said container to be separated from said bag by operation of said tearable connector.

4. The collector of claim 1 wherein said legs in their unstressed condition are spaced apart a distance enabling the legs to be inserted between the labia and beneath the urethra prior to bowing of the legs by inward force on said handles.

5. The collector of claim 1 wherein each of said handles is connected to the second end of respective leg on the same side of said pivot axis as the leg to which said handle is connected, said handles being normally angled away from each so that a force on said handles squeezing them towards each causes said legs to bow in opposite directions.

6. Urine specimen collector for use by females comprising:

a funnel-shaped, urine-impervious bag having a narrow end including an opening therein and a wide end;

a urine specimen collector container having an open neck around which said opening at the narrow end of said bag is sealed;

a tong-like member comprising a pair of resilient legs lying in a common plane, said legs comprising first ends, mounted to each other so as to prevent any substantial movement of said first ends away from each other, said legs further comprising second ends mounted to each other for relative movement about an axis perpendicular to said common plane;

a handle connected to the second end of each of said legs whereby a force in opposite directions on said handles causes the second ends of said legs to pivot away from each other and the legs to bow in opposite directions in said common plane due to their resilience and the interconnection of said first ends of said legs, said wide end of said bag having an opening therein of a length not greater than the lengths of said legs; and means for sealingly connecting the wide end of said bag to said legs on opposite sides of said opening.

7. The collector of claim 6, wherein said resilient legs, and said handle are a molded one piece structure.

* * * * *